(12) United States Patent
Thomson et al.

(10) Patent No.: US 10,324,003 B2
(45) Date of Patent: Jun. 18, 2019

(54) DETECTION OF FRETTING AND/OR SMEARING WITH FALSE-BRINELLING POTENTIAL

(71) Applicant: AKTIEBOLAGET SKF, Göteborg (SE)

(72) Inventors: Allan Thomson, Lanark (GB); Joseph Erskine, Falkirk (GB); Donald Howieson, Livingston (GB)

(73) Assignee: Aktiebolaget SKF, Göteborg (SE)

( * ) Notice: Subject to any disclaimer, the term of this patent is extended or adjusted under 35 U.S.C. 154(b) by 181 days.

(21) Appl. No.: 15/036,458

(22) PCT Filed: Nov. 6, 2014

(86) PCT No.: PCT/EP2014/073914
§ 371 (c)(1),
(2) Date: May 13, 2016

(87) PCT Pub. No.: WO2015/071166
PCT Pub. Date: May 21, 2015

(65) Prior Publication Data
US 2016/0334303 A1    Nov. 17, 2016

(30) Foreign Application Priority Data
Nov. 18, 2013  (GB) .................................. 1320285.8

(51) Int. Cl.
*G01N 29/14*    (2006.01)
*G01M 13/045*    (2019.01)

(52) U.S. Cl.
CPC .......... *G01M 13/045* (2013.01); *G01N 29/14* (2013.01)

(58) Field of Classification Search
CPC .............................. G01M 13/045; G01N 29/14
USPC ............................................................ 73/593
See application file for complete search history.

(56) References Cited

U.S. PATENT DOCUMENTS

| | | | | |
|---|---|---|---|---|
| 4,418,819 | A * | 12/1983 | Shapiro | B65D 71/502 206/216 |
| 4,493,042 | A * | 1/1985 | Shima | G01H 1/003 702/35 |
| 5,072,611 | A | 12/1991 | Budd et al. | |
| 5,922,963 | A * | 7/1999 | Piety | G01M 13/028 702/183 |
| 5,996,230 | A | 12/1999 | Miyazaki et al. | |

(Continued)

FOREIGN PATENT DOCUMENTS

| | | |
|---|---|---|
| CN | 101339094 A | 1/2009 |
| DE | 3623977 A1 | 1/1988 |

(Continued)

OTHER PUBLICATIONS

SKF: "Extend Warning Time and Reduce the Risk of Bearing Failure Using SKF Acoustic Emission Envelping", SKF Application Note CM/P9 13397 EN, Nov. 1, 2012 (Nov. 1, 2012), XP55110810.

*Primary Examiner* — Jacques M Saint Surin
(74) *Attorney, Agent, or Firm* — Bryan Peckjian; SKF USA Inc. Patent Dept.

(57) ABSTRACT

A process for monitoring for the presence of fretting and/or smearing with false brinelling potential in a non-rotating bearing provides the steps of: acquiring acoustic emission data emanating from the non-rotating bearing under an alternating load; and comparing the acoustic emission data with a threshold indicative of fretting and/or smearing.

14 Claims, 4 Drawing Sheets

(56) References Cited

U.S. PATENT DOCUMENTS

| | | | | |
|---|---|---|---|---|
| 6,161,962 | A * | 12/2000 | French | B61F 15/20 |
| | | | | 384/448 |
| 6,634,441 | B2 * | 10/2003 | Palaschenko | E21B 12/02 |
| | | | | 175/39 |
| 7,182,519 | B2 * | 2/2007 | Singh | F01D 17/02 |
| | | | | 384/448 |
| 8,015,876 | B2 * | 9/2011 | El-Bakry | G01H 1/00 |
| | | | | 73/587 |
| 8,438,925 | B2 * | 5/2013 | Klos | G01M 13/045 |
| | | | | 73/587 |
| 8,544,331 | B2 * | 10/2013 | Liang | G01N 29/14 |
| | | | | 73/659 |
| 9,541,128 | B2 * | 1/2017 | Erskine | F16J 15/3296 |
| 9,581,570 | B2 * | 2/2017 | Caicedo | G01N 29/043 |
| 9,683,915 | B2 * | 6/2017 | Ogata | G01M 13/045 |
| 2007/0122070 | A1 * | 5/2007 | Singh | F01D 17/02 |
| | | | | 384/448 |
| 2007/0294049 | A1 * | 12/2007 | Pierce | F03D 7/0224 |
| | | | | 702/151 |
| 2009/0139302 | A1 | 6/2009 | Winter et al. | |
| 2011/0265569 | A1 * | 11/2011 | Ganji | F16C 19/52 |
| | | | | 73/587 |

FOREIGN PATENT DOCUMENTS

| | | |
|---|---|---|
| JP | 2009109267 A | 5/2009 |
| WO | 02/073150 A2 | 9/2002 |
| WO | 2004/085987 A1 | 7/2004 |
| WO | 2012/072984 A2 | 6/2012 |

* cited by examiner

DETECTION OF FRETTING AND/OR SMEARING WITH FALSE-BRINELLING POTENTIAL

CROSS-REFERENCE

This application is the U.S. National Stage of International Application No. PCT/EP2014/073914 filed on Nov. 06, 2014, which claims the benefit of priority from Great Britain Patent Application No. 1320285.8 filed on Nov. 18, 2013, the contents of which are both herein incorporated by reference in their entirety.

FIELD OF THE INVENTION

The present invention relates to the detection of fretting and/or smearing with false-brinelling potential in a roller bearing, and in particular to the use of de-modulated acoustic emission measurements to identify fretting and/or smearing with false-brinelling potential.

BACKGROUND OF THE INVENTION

In order for rolling element bearings to operate in a reliable way, they have to be adequately lubricated. The main purpose of the lubricant is to prevent metallic contact between the rolling elements. The lubricant also protects bearing surfaces against corrosion.

Bearings can suffer damage when they are not rotating.

False-brinelling occurs in a bearing as a result of fretting and/or smearing occuring over time when the bearing is subject to alternating loads, whilst the bearing is not rotating. For example, where a component of a machine such as the blade of a wind turbine is supported in a bearing so that the component may rotate, and the component is subject to cyclic loading whilst the component is not rotating in the bearing.

These alternating loads cause small movements, fretting or smearing movements, between the raceways and the balls or rollers of the bearing which remove the lubrication film between the raceways and the balls or rollers, resulting in metal to metal contact causing surface defects leading to false brinelling. When the bearing is caused to rotate, premature failure is likely to occur.

False-brinelling is a longstanding problem and has been addressed in many ways. False-brinelling is commonly addressed by simply taking the preventitive measure of rotating the bearing periodically so that the lubrication film between the raceway and the balls or rollers is either not removed or is restored. However, there is no accurate method of determining the periodic cycle for rotating a bearing that would otherwise be static.

Structural vibration measurements and displacement measurements have been utilised to quantify false brinelling. However, because many other factors need to be taken into account these techniques often fail to predict false brinelling.

Vibration measurement may be used to detect the presence of false brinelling during rotation of the bearing, but at the point significant vibration occurs the bearing is already damaged.

It would be desirable to be able to predict accurately when false brinelling is likely to occur.

It would be desirable to be able to control a component of a machine mounted in a bearing such that the lubrication layer is restored prior to the occurence of false brinelling.

SUMMARY OF THE INVENTION

It has been found that acoustic emission measurements and measurements derived from acoustic emissions can be associated with the occurence of fretting and/or smearing, which lead to false brinelling. If fretting and/or smearing can be detected, then action can be taken, for example rotating the bearing, so that the lubrication film between the balls or rollers and the raceway may be restored. The fretting and/or smearing action then does not progress to false brinelling.

There are a number of possible sources of acoustic emission associated with fretting and/or smearing. The present invention is concerned with those acoustic emissions associated with fretting and/or smearing that may lead to false brinelling, i.e. those with false brinelling potential.

An acoustic emission is a phenomenon of sound generation in materials under stress that accompanies deformation and fracture processes in the materials. Acoustic emission characteristics are directly dependent on material type, properties and condition. A source of acoustic emission may be continuous or transient and in bearings it is common to have transient acoustic emissions superimposed onto continous acoustic emissions.

In the case of fretting and/or smearing, when these actions remove the lubrication film, metal to metal contact occurs causing an acoustic emission. Where the loading on the bearing is alternating, transient emissions will occur with a period corresponding to the period of the alternating load.

An acoustic emission envelope is a representation of the de-modulated acoustic emission signal. Acoustic emission envelopes having different shapes are associated with different sources. By de-modulating the acoustic emission signal into an envelope it is easier to anaylse the acoustic emission data.

According to first aspect of the invention there is provided a process for monitoring for the presence of fretting and/or smearing with false brinelling potential in a non-rotating bearing comprising the steps of:
  acquiring acoustic emission data emanating from the non-rotating bearing under an alternating load; and
  comparing the acoustic emission data with a threshold indicative of fretting and/or smearing.

The process may include the further step of determining the presence or absence of acoustic emission data indicative of fretting and/or smearing with false brinelling potential.

Advantageously, the process includes the further step of re-establishing the lubrication film in the bearing. The process may comprise the further step of:
  re-acquiring acoustic emission data emanating from the non-rotating bearing under alternating load post re-establishment of the lubrication film in the bearing.

The process according may comprise the further step of:
  determining the presence or absence of acoustic emission data indicative of fretting and/or smearing with false brinelling potential in the re-aquired acoustic emission data.

Preferably, the acoustic emission data is demodulated, and more preferably, the de-modulated acoustic emission data is in the form of an acoustic emission envelope.

Advantageously, the step of comparing the acoustic emission data with a threshold indicative of fretting and/or smearing comprises establishing the number of counts exceeding the threshold and may comprise the further step of comparing the number of counts exceeding the threshold with an alarm number of counts indicating fretting and/or smearing.

The process may comprise the step of establishing the period of the load cycle on the non-rotating bearing and correlating the acoustic emission data with the load cycle period.

The step of correlating the acoustic emission data with the load cycle period may comprise the step of obtaining the acoustic emission period.

Preferably, the step of determining the presence or absence of acoustic emission data indicative of fretting and/or smearing with false brinelling potential in the re-aquired acoustic emission data comprises establishing the synchronisity of the load cycle period with the acoustic emission period in re-acquired data, and more preferably establishing whether or not the load cycle period is synchronised with the acoustic emission period in the re-acquired data. If the load cycle period and the acoustic emission period in the re-acquired data are not synchronised, this is an indication that the acoustic emission data indicative of fretting and/or smearing in the first acquired data did have false brinelling potential, i.e. was occuring in the bearing due to degradation of the lubrication layer.

Advantageously, the process comprises the step of issuing a signal indicating the presence of fretting and/or smearing with false-brinelling potential.

Preferably, the issued signal is an alarm and/or control signal.

Preferably, the step of re-establishing the lubrication film in the bearing comprises rotating the bearing.

According to another aspect of the invention there is provided an apparatus including a bearing supporting a component, an acoustic emission sensor positioned in relation to the bearing to detect an acoustic emission emanating from the bearing and a condition monitoring device communicating with the acoustic emission sensor, wherein the condition monitoring device is configured to perform the process of the first aspect of the invention.

Advantageously, the apparatus further comprises an actuator configured to rotate the bearing. The actuator may be one of: a driven shaft, a piston and cylinder, and a linear actuator.

BRIEF DESCRIPTION OF THE DRAWINGS

In the drawings, which illustrate preferred embodiments of a process and apparatus according to the invention, and are by way of example.

DETAILED DESCRIPTION OF THE INVENTION

Figure 1:
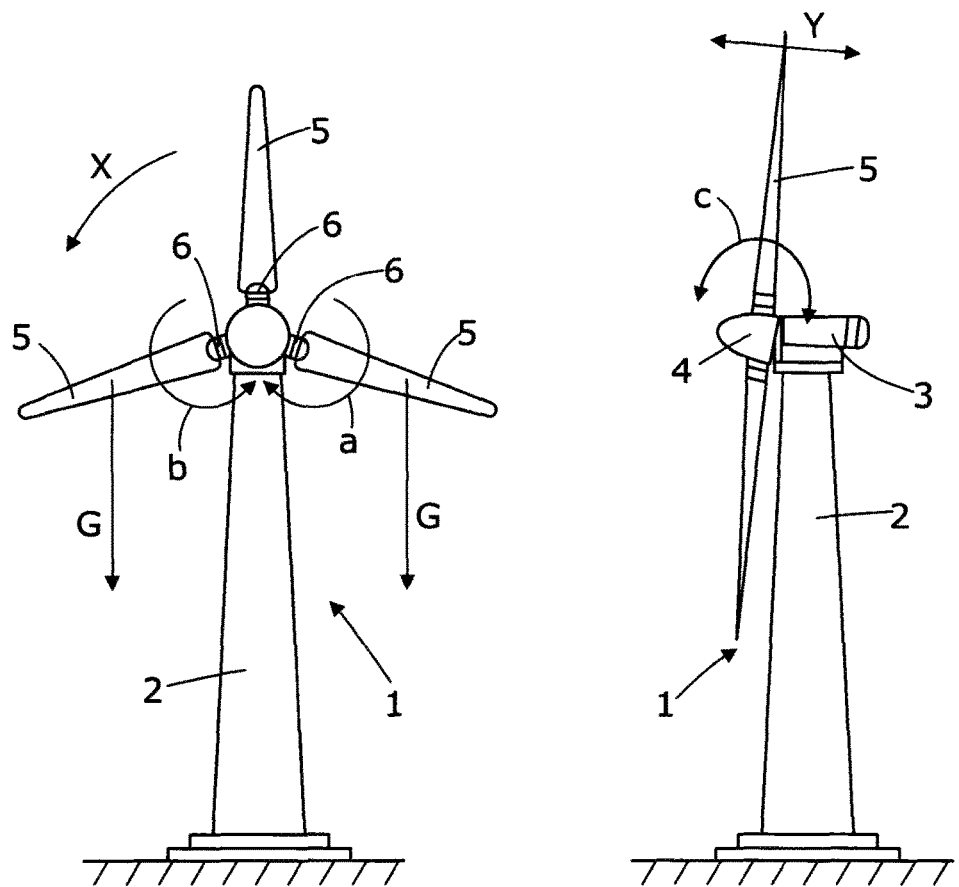
FIG. 1 illustrates front and side views of a wind turbine.

The wind turbine 1 illustrated in FIGS. 1 comprises a tower 2, a nacelle 3 housing a gearbox and generator, and a rotor 4 mounting three blades 5.

Each blade 5 is attached to the rotor by a bearing 6 which allows the pitch of the blade to be adjusted. The bearing 6 is likely to suffer from false brinelling because the pitch of the blades 5 is not adjusted often and the blades are subject to cyclic loads.

For example, with each rotation in the direction X of the rotor 4 the effect of gravity, indicated by arrow G, on a single blade 5 changes from being negative on the upstroke to positive on the down stroke. In the upstroke the moment on the bearing 6 is indicated by arrow a. In the downstroke the moment on the bearing 6 is indicated by arrow b.

The blades 5 also oscillate in the direction Y causing a changing moment on the bearing 6 indicated by arrow c. This oscillation can occur while the rotor is turning or while it is stationary.

Fretting and/or smearing actions in a bearing produce acoustic emissions. However, other fretting and/or smearing actions for example from the bearing seat also produce an acoustic emission. In order to identify acoustic emissions as being associated with fretting action in the bearing raceways, that is with false brinelling potential, it is therefore necessary to separate out acoustic emissions associated with the bearing raceway from other acoustic emissions associated with the bearing.

In the present example, each bearing 6 is instrumented with load sensor and an acoustic emission sensor. The acoustic emission sensor may be attached to a bearing ring or a bearing housing, or another fixed structure to which the bearing is mounted.

When the lubrication film in the bearing that separates the rolling contact surfaces becomes so thin that asperity contact (metal to metal contact) occurs, these asperity contacts give rise to acoustic emission. The characteristics of the acoustic emission are indicative of the degree of asperity contact between the rolling contact surfaces of the bearing.

Figure 2:
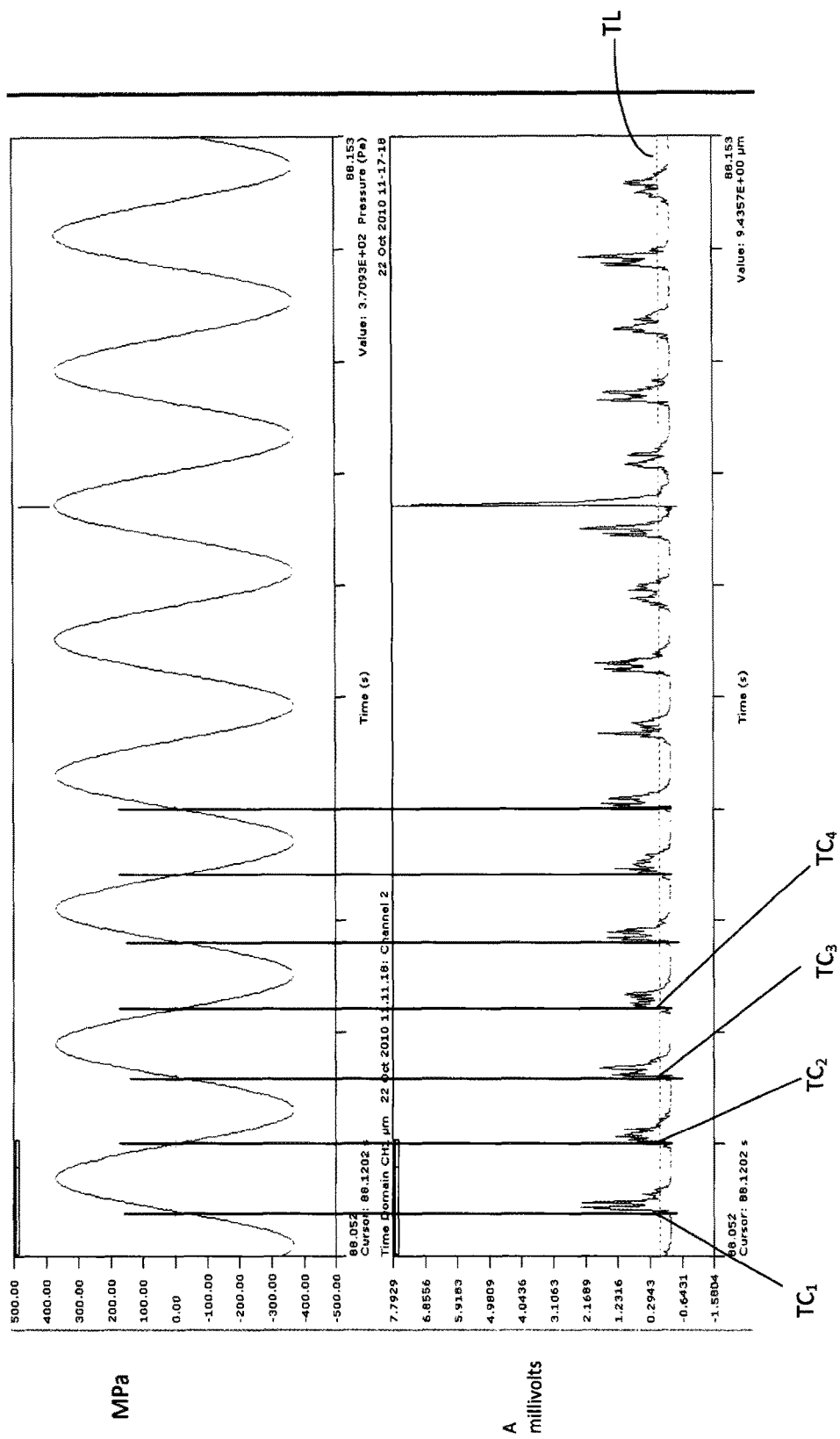
FIG. 2 show graphs of load versus time and the corresponding acoustic emission envelope signal.

In FIG. 2 the upper plot is of load versus time on one of the bearings 6. As can be seen the load on the bearing 6 cycles between positive and negative as the rotor 4 rotates. The lower plot illustrates the acoustic emission envelope with time.

It is clear from the two plots that most of the bursts of acoustic emission activity are associated with the cyclical change of load on the bearing.

The period of the load and fluctuations therein may be determined from monitorable parameters of the apparatus of which the bearing 6 forms a part, rather than monitoring the load itself. For example, in a wind turbine, where it is understood that fluctuations in load on the bearing 6 are associated with rotation of the rotor 4, the period of the load fluctuations may be derived from the speed of rotation of the rotor. Obviously, this would require a measurement of speed of rotation of the rotor. This measurement may be available from other monitoring equipment associated with the wind turbine 1.

Figure 3:
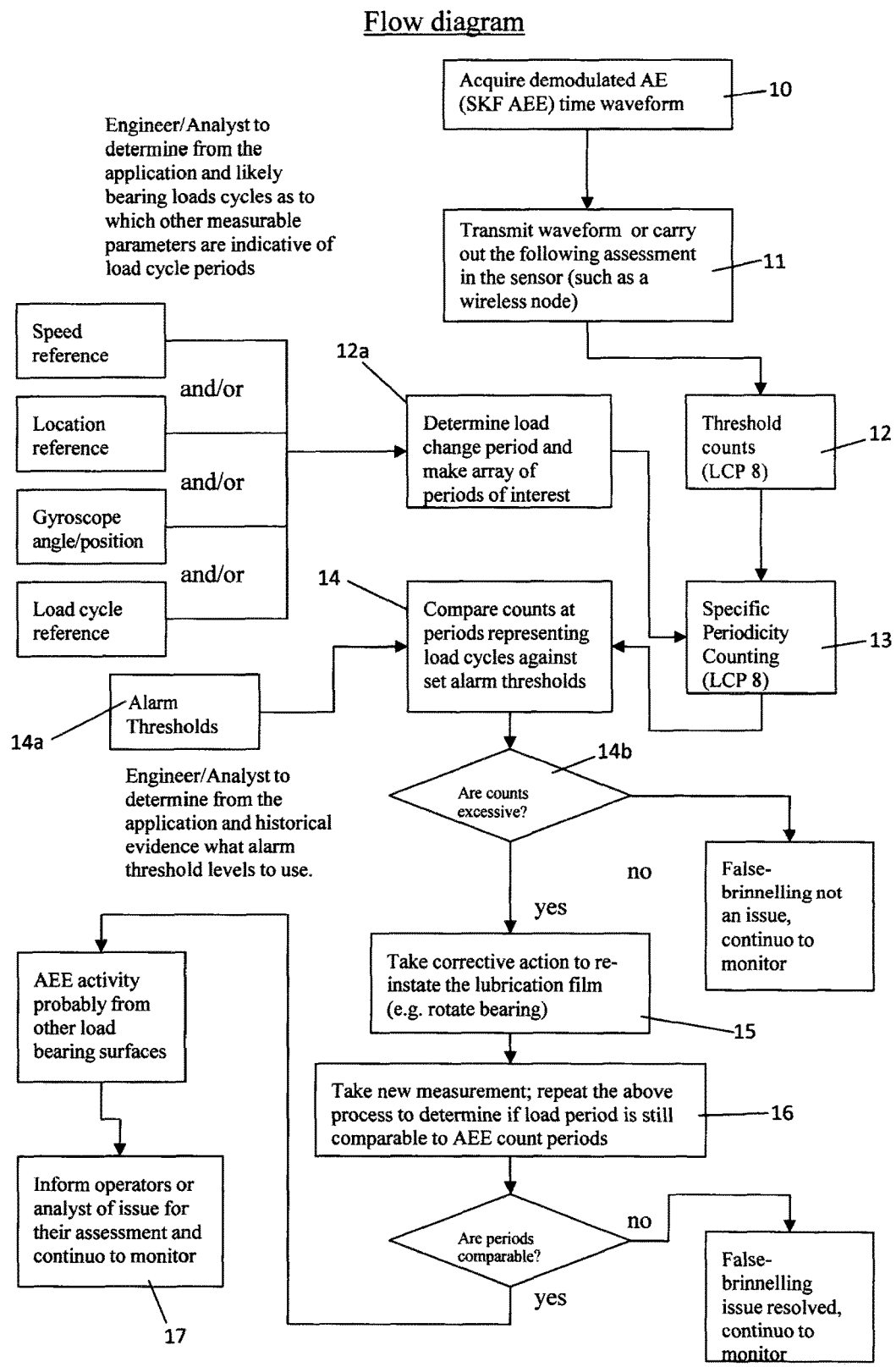
FIG. 3 is a flow diagram illustrating the process of the invention.

The flow diagram shown in FIG. 3 illustrates how detected acoustic emission activity is identified as indicating a false brinelling issue. The steps set out in the flow diagram are carried on in a computer device.

In step 10 an acoustic emission detected by the acoustic emission sensor is demodulated to provide an acoustic emission envelope time waveform.

In step 11 the waveform acquired in step 10 is either transmitted to another processor for further processing according to the subsequent steps, or those processing steps are performed in the sensor.

In step 12 the waveform of AEE events is subjected to threshold based signal processing. The waveform is compared with a threshold to establish a number of counts exceeding the threshold as explained in greater detail below with reference to FIG. 2.

The lower plot in FIG. 2 shows the AEE signal amplitude A on the ordinate v time T on the abscissa. The line TL represents a threshold level of acoustic emission amplitude that represents possible fretting or smearing. The number of counts is the number of crossings of the line TL that represent an acoustic event, that is $TC_1$, $TC_2$, $TC_3$, $TC_4$ ... $TC_n$.

The time between acoustic emission events, that is the time between the first rising threshold crossing $TC_1$ of an acoustic emission event and the first rising threshold crossing $TC_2$ of the next acoustic emission event is measured, this representing the period between acoustic emission events.

To assist in the analysis the processed signal resulting from step 12 is associated with the load change period in step 13, the load change period being determined in step 12a by reference to one or more measurable parameters that are indicative of load cycle periods, as described below.

The references of speed, location, gyroscope angle/position and load cycle are possible inputs that are indicative of the load cycle period. Other measurable parameters indicative of load cycle periods may be used in addition to or instead of the aforementioned reference parameters. The load change period is determined from one or more of these inputs in step 12a.

The graphs shown in FIG. 2 illustrate the load cycle associated with the AEE waveform.

In step 14 the number of counts exceeding the threshold TL is compared with an alarm threshold input 14a. The alarm threshold is set by an analyst or engineer from the particular application, historical evidence and modelling data, for example a loading cycle on a non-rotating bearing may be monitored in the laboratory until false-brinelling does occur and the acoustic emission characteristics recorded and analysed. For a particular application the alarm threshold may be a particular number of counts exceeding the threshold TL. For example, over an acquisition period of five rotations it may be expected that two or three acoustic emission events may coincide with the loading cycle on the bearing. The alarm threshold may in that case be set at five, because if there are five acoustic events coniciding with the loading cycle on the bearing this is unlikely to be coincidental and is likely to due to fretting or smearing in the bearing associated with the changing load on the bearing.

In step 14b a determination as to whether the alarm threshold is exceeded or not is made. If the alarm threshold is not exceeded, that is a determination that there is no false brinelling issue and monitoring according to steps 10 to 14 continues.

On the other hand, if the alarm threshold is exceeded that is an initial indication that there may be a false brinelling issue, i.e. the acoustic emission indicates fretting and/or smearing that may have false brinelling potential. However, it is not a determination of that.

In order to confirm that the fretting or smearing indicated is fretting or smearing that could develop into false brinelling it needs to be ascertained that the fretting or smearing is occuring in the bearing raceway, not another part of the bearing.

This can be achieved by changing the condition of the monitored bearing and performing steps 10 to 13.

In step 15 action is taken to change the condition of the monitored bearing. For example, the bearing may be rotated to re-establish the lubrication film.

Following the re-performance of steps 10 to 13, in step 16 the load period is compared with the AEE count period. If the two periods are not synchronised this indicates that there was a false brinelling issue and it has been resolved, because the lubrication layer has been re-established and hence fretting and/or smearing is no longer occuring. Of course monitoring should continue so that when the condition in the bearing changes such that fretting and/or smearing is occuring, this can be detected and rectified.

If the load period and the AEE count period remains the same then the AEE waveform must be due to some other issue. In step 17 an operator is informed of that there is an issue other than false brinelling so that the issue may be investigated.

The method of detecting false brinelling may be incorporated into a control system for the operation of a machine, such as a wind turbine.

Figure 4:
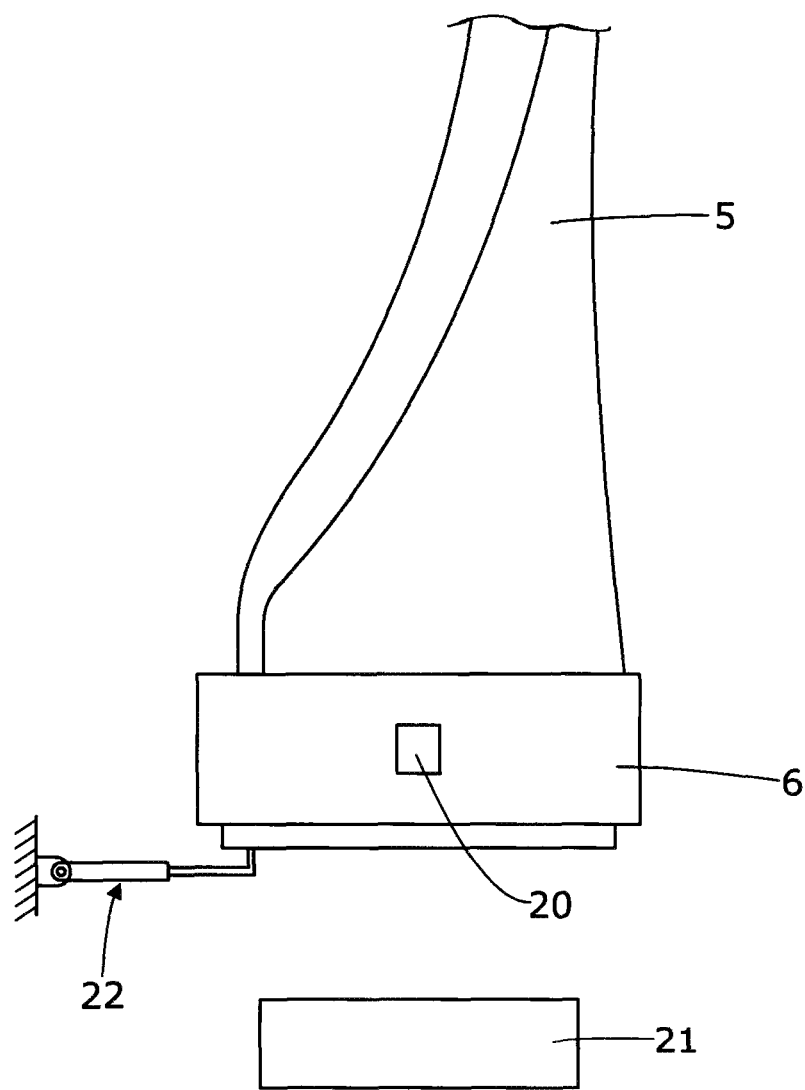
FIG. 4 is a schematic representation of a bearing of the wind turbine illustrated in FIG. 1.

For example, in the wind turbine 1 illustrated in FIG. 1, each bearing 6 may be equipped with one or more acoustic emission sensors 20 as shown in FIG. 4, which are connected to a processor, condition monitoring device 21 which may form part of a larger wind turbine management system for example. The processor is programmed to perform the steps set out in the flow diagram illustrated in FIG. 3. The wind turbine may be equipped with an actuator 22 to rotate the blade 5, which causes the bearing 6 to rotate. The process of the invention provides for a signal to be issued to command the actuator to move in order to rotate the bearing 6, that is to take the corrective action identified in step 15. The actuator 22 need not be of the piston and cylinder type. Any suitable type of actuator may be used. For example, the actuator may be a shaft driven. The shaft may be powered electrically, hydraulically, aerodynamically or hydrodynamically.

Whilst the application described is in relation to a wind turbine, there are many situations where non-rotating bearings are subject to cyclic loads. For example, objects mounted on floating vessels, on vehicles, non-rigid structures, objects situated proximate sources of vibration transmitted to the object through foundations, pipework or other media, and where environmental conditions place changing load conditions on a static bearing, such as waves, current, wind and temperature oscillations.

The invention is not limited to a process having all the steps described in the preferred embodiments. There may be utility in utilising a process with more limited steps as defined in the claims.

Individual technical features of the illustrated embodiments are not limited to use in those embodiments, and may where suitable, be used with any embodiment falling within the scope of the claims.

The invention claimed is:

1. A process for monitoring for the presence of fretting and/or smearing with false brinelling potential in a non-rotating bearing comprising the steps of:
   acquiring acoustic emission data emanating from the non-rotating bearing under an alternating load; and
   comparing the acoustic emission data with a threshold indicative of fretting and/or smearing, the step of comparing the acoustic emission data comprising establishing the number of counts exceeding the threshold.

2. The process according to claim 1, further comprising the step of determining the presence or absence of acoustic emission data indicative of fretting and/or smearing with false brinelling potential.

3. The process according to claim 1 further comprising the step of establishing a lubrication film in the bearing.

4. The process according to claim 3, further comprising the step of:
   re-acquiring acoustic emission data emanating from the non-rotating bearing under alternating load post re-establishment of the lubrication film in the bearing.

5. The process according to claim 4, further comprising the step of:

determining the presence or absence of acoustic emission data indicative of fretting and/or smearing with false brinelling potential in the re-acquired acoustic emission data.

6. The process according to claim 1, wherein the acoustic emission data is demodulated.

7. The process according to claim 6, wherein the demodulated acoustic emission data is in the form of an acoustic emission envelope.

8. The process according to claim 1, further comprising the step of comparing the number of counts exceeding the threshold with an alarm number of counts indicating fretting and/or smearing.

9. The process according to claim 1, further comprising the step of establishing the period of the load cycle on the non-rotating bearing and correlating the acoustic emission data with the load cycle period.

10. The process according to claim 9, wherein the step of correlating the acoustic emission data with the load cycle period further comprises the step of obtaining the acoustic emission period.

11. The process according to claim 1, further comprising the step of issuing a signal indicating the presence of fretting and/or smearing with false-brinelling potential.

12. The process according to claim 11, wherein the issued signal is an alarm and/or control signal.

13. The process according to claim 1, wherein the step of re-establishing the lubrication film in the bearing further comprises rotating the bearing.

14. A process for monitoring for the presence of fretting and/or smearing with false brinelling potential in a non-rotating bearing comprising the steps of:
   acquiring acoustic emission data emanating from the non-rotating bearing under an alternating load;
   comparing the acoustic emission data with a threshold indicative of fretting and/or smearing;
   establishing a lubrication film in the bearing;
   re-acquiring acoustic emission data emanating from the non-rotating bearing under alternating load post re-establishment of the lubrication film in the bearing;
   determining the presence or absence of acoustic emission data indicative of fretting and/or smearing with false brinelling potential in the re-acquired acoustic emission data;
   establishing the period of the load cycle on the non-rotating bearing and correlating the acoustic emission data with the load cycle period, and wherein
   the step of determining the presence or absence of acoustic emission data indicative of fretting and/or smearing with false brinelling potential in the re-acquired acoustic emission data comprises establishing the synchronicity of the load cycle period with the acoustic emission period in re-acquired data.

* * * * *